US005510624A

United States Patent [19]

Zaluzec

[11] Patent Number: 5,510,624
[45] Date of Patent: Apr. 23, 1996

[54] SIMULTANEOUS SPECIMEN AND STAGE CLEANING DEVICE FOR ANALYTICAL ELECTRON MICROSCOPE

[75] Inventor: Nestor J. Zaluzec, Bolingbrook, Ill.

[73] Assignee: The University of Chicago, Chicago, Ill.

[21] Appl. No.: 522,618

[22] Filed: Sep. 1, 1995

[51] Int. Cl.$^6$ ............................................ H01J 37/067
[52] U.S. Cl. ............................................... 250/441.11
[58] Field of Search ........................ 250/441, 11, 440.11, 250/370, 371, 492.2, 492.21, 492.3

[56] References Cited

U.S. PATENT DOCUMENTS 5,312,519  5/1994  Sakai et al. .................... 250/441.11

OTHER PUBLICATIONS

The Use of Plasma–Cleaning for the Preparation of Clean Electron–Transparent Thin Foils, Zandbergen et al., ICEM 13–Paris, 17–22 Jul. 1994, pp. 1003–1004.

Use of Chemically Reactive Gaseous Plasmas in Preparation of Specimens for Microscopy, Richard S. Thomas, Techniques and Applications of Plasma Chemistry, A Wiley-–Interscience Publication, 1974, Chapter 8, pp. 255–346.

Primary Examiner—Jack I. Berman
Assistant Examiner—Kiet T. Nguyen
Attorney, Agent, or Firm—Mason, Kolehmainen, Rathburn & Wyss

[57] ABSTRACT

An improved method and apparatus are provided for cleaning both a specimen stage, a specimen and an interior of an analytical electron microscope (AEM). The apparatus for cleaning a specimen stage and specimen comprising a plasma chamber for containing a gas plasma and an air lock coupled to the plasma chamber for permitting passage of the specimen stage and specimen into the plasma chamber and maintaining an airtight chamber. The specimen stage and specimen are subjected to a reactive plasma gas that is either DC or RF excited. The apparatus can be mounted on the analytical electron microscope (AEM) for cleaning the interior of the microscope.

16 Claims, 4 Drawing Sheets

SIMULTANEOUS SPECIMEN AND STAGE CLEANING DEVICE FOR ANALYTICAL ELECTRON MICROSCOPE

CONTRACTUAL ORIGIN OF THE INVENTION

The United States Government has rights in this invention pursuant to Contract No. W-31-109-ENG-38 between the United States Government and Argonne National Laboratory.

BACKGROUND OF THE INVENTION

1. Field of the Invention

The present invention relates to analytical electron microscope applications, and more particularly to a method and apparatus for cleaning a specimen stage and specimen for viewing in an analytical electron microscope (AEM).

2. Description of the Prior Art

The ability to characterize materials by analytical electron microscopy is limited by the ability to detect and analyze constituents present in very small samples. Surface borne contaminants or surface films interacting with the high energy incident electron probe can create deposits on the surface of a sample interfering with the electron probe and thus adversely affect or prohibit accurate analysis.

Contaminants typically are introduced by one of four ways including the specimen, the specimen stage, carried into the chamber by the evacuation system, or are present on the internal components of the instrument. Contaminants from the evacuation system can usually be reduced by the manufacturer of the instrument, the first two items cannot.

The preparation of inorganic specimens (metals, ceramics, semiconductors, etc.) frequently involves chemical or electrochemical polishing, or ion milling followed by solvent rinsing and air drying. This typically leaves a residual contaminant or film on the specimen surface. Cleaning of specimen stage is also sometimes followed by rinsing of the stage with various organic solvents. Even though the organic solvents evaporate, a small amount of residue may typically remain on the sample and stage.

Also improper or poor techniques used to store both the specimens and/or stages prior to insertion into the microscope can introduce additional residues. While the majority of the films created in these processes dissipate, a small amount generally remains on surfaces and is sufficient to cause problems when the specimen is subsequently examined in modern analytical microscopes.

Although these residues are widely distributed and generally are at low concentrations on the various surfaces, some materials can become mobile in the microscope environment and are attracted to the periphery of any focused electron probe, forming deposits. Since these contaminants can travel large distances over the surface of a specimen, it is important to remove or immobilize these species as much as possible prior to an analysis without disturbing the microstructure of the specimen.

It has been well documented that low temperature (<50° C.) plasmas of various ionized gases can be used to reactively etch/ash organic materials found on the surface of materials. This has been used in the industrial community to clean semiconductor wafers and other bulk materials for many years. In that procedure, typically the material is placed in an RF cavity or a DC cavity with a flowing reactive gas. The nature of the gas selected is chosen based upon the desired effect. Oxygen or argon is generally used, however, specific gases ($BCl_3$, $CF_4$) may be used to tailor the reaction for the desired effect.

It is an object of the present invention to provide an improved method and apparatus for cleaning both a specimen stage and a specimen or any other item inserted into the vacuum system of an analytical electron microscope (AEM).

It is another object of the present invention to provide such an improved method and apparatus including a low temperature plasma.

It is another object of the present invention to provide such an improved method and apparatus including a low temperature reactive gas plasma that provides reliable and effective operation.

It is another object of the present invention to provide such an improved method and apparatus including a low temperature reactive gas plasma that overcomes many of the disadvantages of prior art arrangements.

SUMMARY OF THE INVENTION

In brief, these and other objects and advantages of the invention are provided by an improved method and apparatus for cleaning both a specimen stage, a specimen and an interior of an analytical electron microscope (AEM). The apparatus for cleaning a specimen stage and specimen comprising a plasma chamber for containing a gas plasma and an air lock coupled to the plasma chamber for permitting passage of the specimen stage and specimen into the plasma chamber and maintaining an airtight chamber. The specimen stage and specimen are subjected to a reactive plasma gas that is either DC or RF excited.

BRIEF DESCRIPTION OF THE DRAWING

The present invention together with the above and other objects and advantages may best be understood from the following detailed description of the preferred embodiments of the invention illustrated in the drawing, wherein.

DETAILED DESCRIPTION OF THE PREFERRED EMBODIMENTS

In accordance with the invention, a technique has been developed which allows simultaneous cleaning of a sample and a specimen stage of a transmission electron microscope which minimizes and in some cases eliminates contamination and films from the surface of inorganic specimens during analysis by analytical electron microscopy (AEM). The procedure, which involves subjecting the specimen and stage to a reactive plasma gas (either DC or RF excited) is carried out prior to inserting the specimen and stage into the AEM and can be extended for use on all types of electron microscopes where the sample and stage are loaded external to the instrument.

Figure 1:
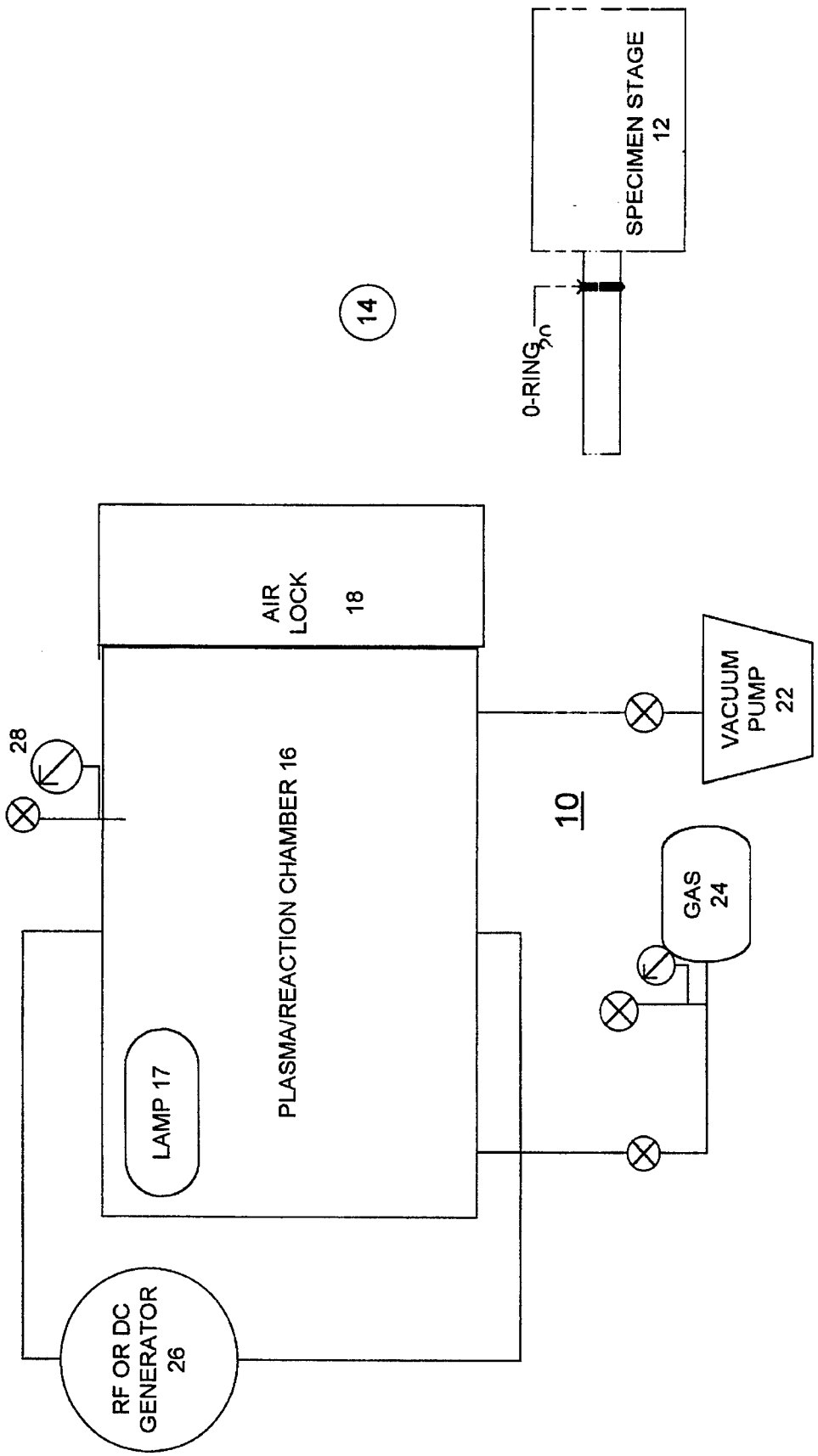
FIG. 1 is a schematic and block diagram representation of a plasma cleaner for cleaning both a specimen stage and a specimen in accordance with the present invention.
Figure 2:
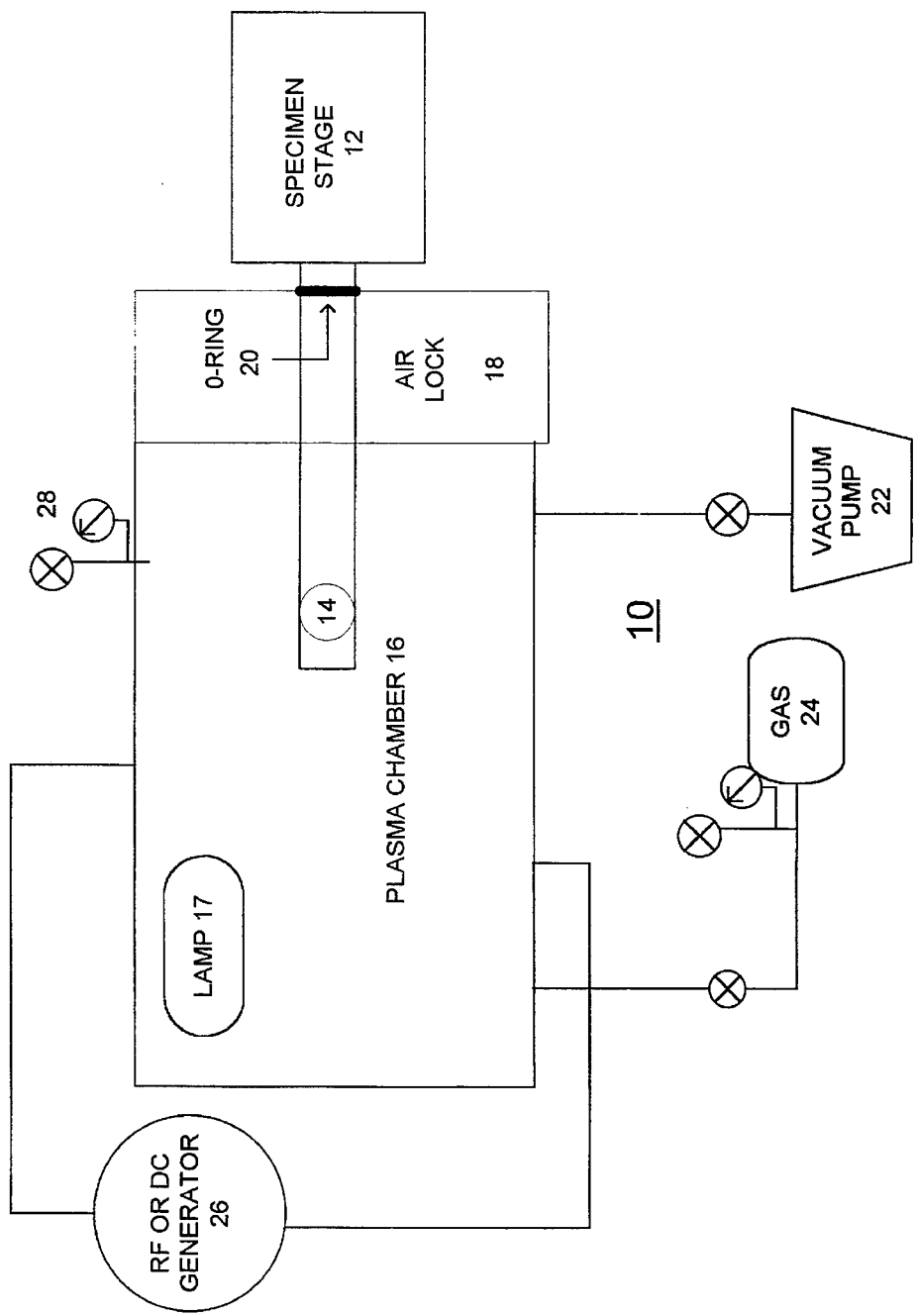
FIG. 2 is similar to FIG. 1 illustrating the specimen stage and the specimen inside the plasma cleaner.

Having reference now to the drawings, in FIG. 1 there is shown a plasma cleaner generally designated by the reference character 10 for cleaning both a specimen stage 12 and a specimen 14 for viewing in an analytical electron microscope (AEM). As used in the following description and claims, an analytical electron microscope (AEM) is any instrument which uses an electron beam in a vacuum to produce a signal from a point on the specimen. The signal may be an image, a diffraction pattern, or any spectroscopic information.

In accordance with the method of the invention used for AEM, instead of just subjecting the material of interest, i.e., the specimen 14 to a plasma for cleaning, the entire stage 12 and sample 14 are cleaned in a plasma chamber 16. This was accomplished by providing an airlock 18 to a conventional plasma reactor. An O-ring 20 is carried by the specimen stage 12 to provide an airtight seal with the airlock 18.

Figure 3:
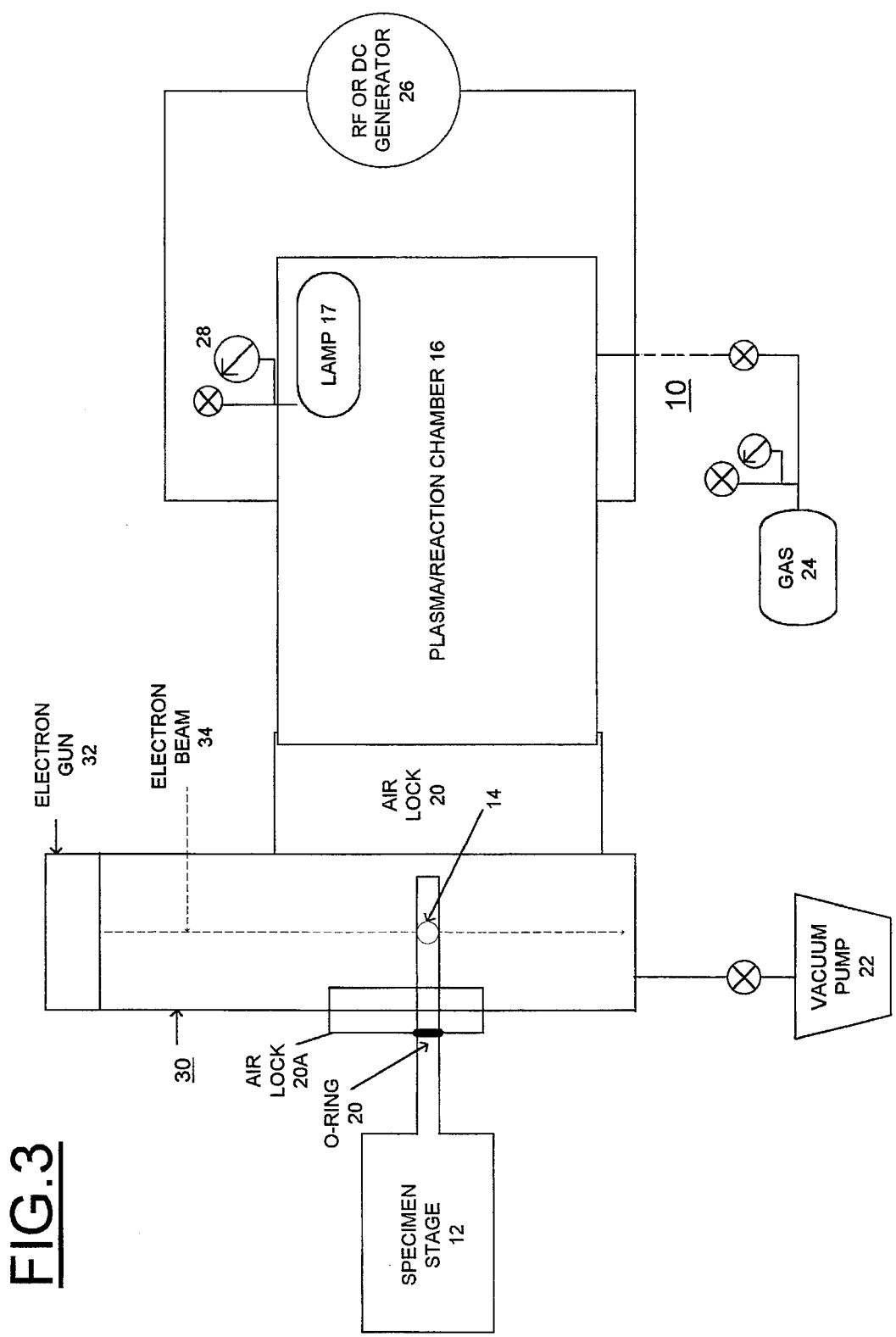
FIG. 3 is a schematic and block diagram representation of a plasma cleaner attached to an analytical transmission electron microscope for cleaning a specimen stage, a specimen and internal microscope components in accordance with the present invention.
Figure 4:
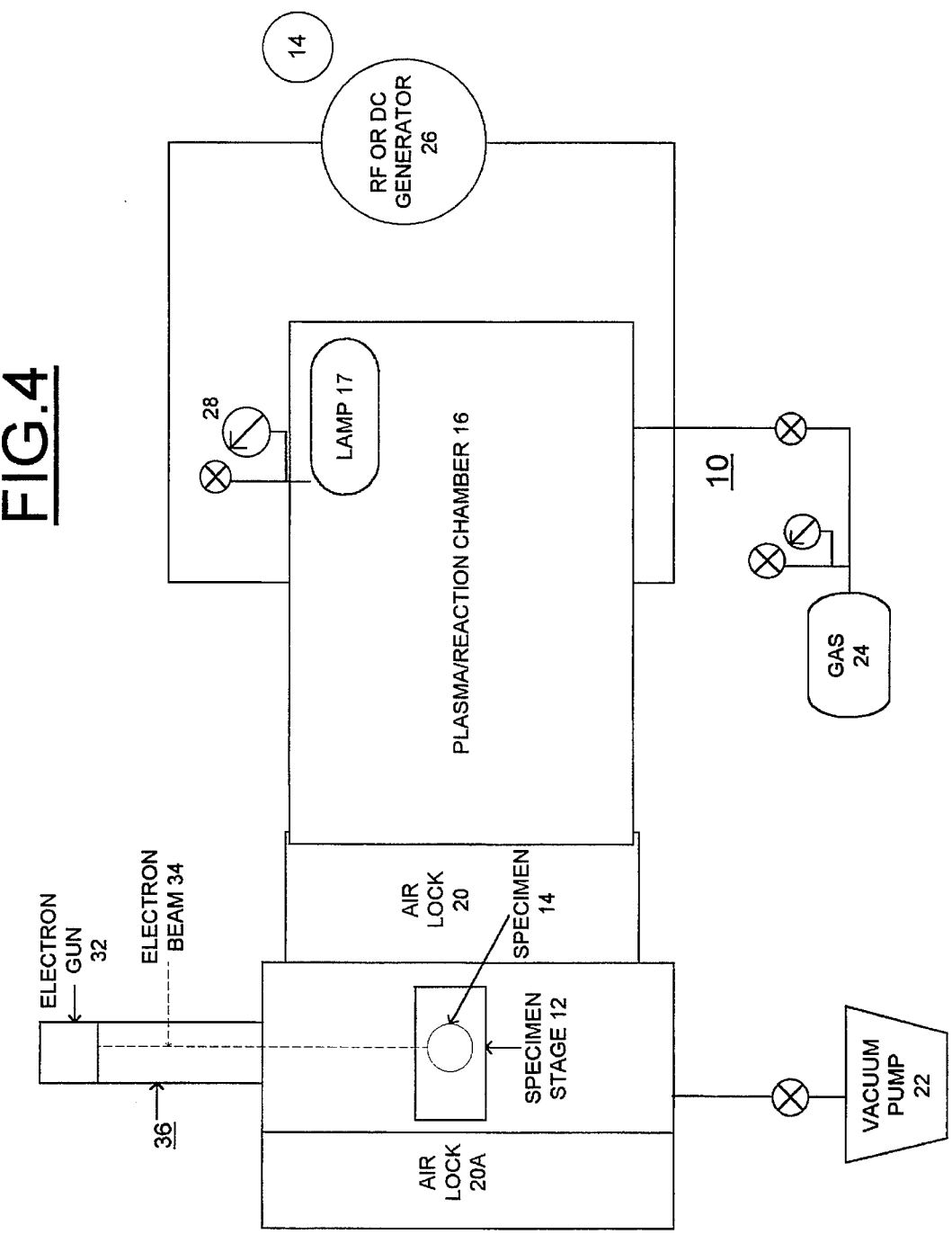
FIG. 4 is similar to FIG. 3 illustrating the plasma cleaner attached to an analytical scanning electron microscope for cleaning a specimen stage, a specimen and internal microscope components.

Apparatus 10 of the present invention includes a low temperature plasma chamber 16 modified with the air lock 18 so that it will accept the specimen stage 12 together with the specimen 14 mounted on it. The air lock 18 advantageously is arranged so that specimen stages 12 from a variety of commercially available microscopes will fit through it. The plasma chamber 16 optionally includes the addition of an ultraviolet (UV) or halogen lamp 17. The plasma chamber 16 can be mounted either on or within the microscope so that the stage 12, the mounted specimen 14, and the interior of the microscope are cleaned, as illustrated in FIGS. 3 and 4.

The plasma chamber 16 can be adapted for use with a range of microscopy techniques including optical microscopy and scanning electron microscope (SEM).

The airlock 18 is arranged such that conventional side entry specimen stages 12 from an analytical electron microscope (with specimen loaded), may be directly inserted into the plasma. The specimen and stage are then plasma etched or ashed with the selected gas and subsequently inserted into the electron microscope. If during the course of an investigation a specimen is observed to begin to contaminate, the experiment may be momentarily halted, the stage 12 removed from the microscope, plasma cleaned a second time and then reinserted for continued experimentation. Cleaning time is typically 10 minutes, and specimens that typically contaminate in minutes can after treatment be studied for several hours before problems develop and retreatment is needed.

A vacuum pump 22 is coupled to the plasma chamber 16 for evacuating the chamber. A gas source 24 is coupled to the plasma chamber 16 for backfilling the chamber with a gas, such as argon (Ar) or oxygen ($O_2$). A radio frequency (RF) or DC source 26 is provided for exciting the gas within the plasma chamber 16 for gas plasma cleaning treatment of the specimen stage 12 and the specimen 14. A pressure gauge 28 is coupled to the plasma chamber 16 for monitoring gas pressure within the chamber.

Referring also to FIGS. 3 and 4, there are shown the plasma cleaner 10 attached to an analytical electron microscope for simultaneously plasma cleaning the internal microscope components with the specimen stage 12 and specimen 14. In FIGS. 3 and 4, identical reference numbers are used for similar components. In FIG. 3, the plasma cleaner 10 is shown attached to an analytical transmission electron microscope generally designated by the reference character 30. An electron gun 32 generates an electron beam 34 in the electron-optical microscope column and vacuum system. An available microscope air lock 20A on the analytical transmission electron microscope 30 is used for inserting the specimen 14 and specimen stage 12. Specimen stage 12 is mounted on the electron-optical microscope column. The vacuum pump 22 may be provided by an available vacuum pump of the analytical transmission electron microscope 30. In FIG. 4, the plasma cleaner 10 is shown attached to an analytical scanning electron microscope generally designated by the reference character 36.

While the present invention has been described with reference to the details of the embodiments of the invention shown in the drawing, these details are not intended to limit the scope of the invention as claimed in the appended claims.

What is claimed is:

1. Apparatus for cleaning a specimen stage and specimen for viewing in an analytical electron microscope (AEM) comprising:

plasma chamber means for containing a gas plasma; and air lock means coupled to said plasma chamber means for permitting passage of the specimen stage and specimen into the plasma chamber means and for maintaining an airtight chamber.

2. Apparatus for cleaning a specimen stage and specimen as recited in claim 1 wherein said plasma chamber means includes:

means for evacuating said plasma chamber means;

means for flowing a gas into said plasma chamber means; and means for exciting said gas with either a radio frequency (RF) or direct current (DC) signal.

3. Apparatus for cleaning a specimen stage and specimen as recited in claim 2 wherein said gas is oxygen and said gas plasma is an oxygen gas plasma.

4. Apparatus for cleaning a specimen stage and specimen as recited in claim 2 wherein said gas is argon and said gas plasma is an argon gas plasma.

5. Apparatus for cleaning a specimen stage and specimen as recited in claim 1 wherein said plasma chamber means includes:

a light source within said plasma chamber means.

6. Apparatus for cleaning a specimen stage and specimen as recited in claim 1 wherein said specimen stage carries an O-ring for air-tight engagement with said air lock means.

7. Apparatus for cleaning a specimen stage and specimen as recited in claim 1 further includes means for mounting said plasma chamber to the analytical electron microscope (AEM) for cleaning an interior of the AEM.

8. A method for cleaning a specimen stage and specimen for viewing in an analytical electron microscope (AEM) comprising the steps of:

providing a plasma chamber with an airlock for permitting passage of the specimen stage and specimen into the plasma chamber means and for maintaining an airtight chamber;

inserting the specimen stage and specimen into the plasma chamber and cleaning the specimen stage and specimen utilizing a gas plasma.

9. A method for cleaning a specimen stage and specimen as recited in claim 8 further includes the step of mounting said plasma chamber to the analytical electron microscope (AEM) for cleaning an interior of the AEM.

10. A method for cleaning a specimen stage and specimen as recited in claim 8 wherein the step of cleaning the specimen stage and specimen utilizing a gas plasma includes the step of:

flowing an oxygen gas into the plasma chamber.

11. A method for cleaning a specimen stage and specimen as recited in claim 8 wherein the step of cleaning the specimen stage and specimen utilizing a gas plasma includes the step of:

flowing an argon gas into the plasma chamber.

12. A method for cleaning a specimen stage and specimen as recited in claim 8 wherein the step of cleaning the specimen stage and specimen utilizing a gas plasma includes the steps of:

placing the specimen stage and the specimen into the plasma chamber;

flowing an oxygen gas into the plasma chamber; and exciting the oxygen gas plasma with either a radio frequency (RF) or direct current (DC) signal.

13. A method for cleaning a specimen stage and specimen as recited in claim 8 wherein the step of cleaning the specimen stage and specimen utilizing a gas plasma includes the steps of:

placing the specimen stage and the specimen into the plasma chamber;

flowing an argon gas into the plasma chamber; and exciting the argon gas plasma with either a radio frequency (RF) or direct current (DC) signal.

14. A method for cleaning a specimen stage and specimen as recited in claim 8 wherein the step of cleaning the specimen stage and specimen utilizing a gas plasma includes applying a gas plasma for a selected time period.

15. A method for cleaning a specimen stage and specimen as recited in claim 14 wherein said selected time period is in a range between 5 minutes and 10 minutes.

16. A method for cleaning a specimen stage and specimen as recited in claim 14 wherein said selected time period is in a range between 2 hours and 5 hours.

\* \* \* \* \*